United States Patent
McDermott et al.

(10) Patent No.: US 9,987,204 B2
(45) Date of Patent: Jun. 5, 2018

(54) SOLID COSMETIC MAKEUP COMPOSITION

(75) Inventors: Padraig McDermott, Meudon (FR); Gwenola Le Gars, Paris (FR); Catherine Sautel, L'Hay les Roses (FR)

(73) Assignee: L'OREAL, Paris (FR)

( * ) Notice: Subject to any disclaimer, the term of this patent is extended or adjusted under 35 U.S.C. 154(b) by 408 days.

(21) Appl. No.: 13/824,169

(22) PCT Filed: Sep. 16, 2011

(86) PCT No.: PCT/IB2011/054047
§ 371 (c)(1),
(2), (4) Date: Mar. 15, 2013

(87) PCT Pub. No.: WO2012/035512
PCT Pub. Date: Mar. 22, 2012

(65) Prior Publication Data
US 2013/0253072 A1 Sep. 26, 2013

Related U.S. Application Data

(60) Provisional application No. 61/390,297, filed on Oct. 6, 2010.

(30) Foreign Application Priority Data

Sep. 17, 2010 (FR) ...................... 10 57469

(51) Int. Cl.
A61Q 1/00 (2006.01)
A61Q 1/12 (2006.01)
A61K 8/25 (2006.01)
A61K 8/26 (2006.01)
A61K 8/891 (2006.01)
A61K 8/898 (2006.01)
A61K 8/96 (2006.01)
A61Q 1/10 (2006.01)

(52) U.S. Cl.
CPC ............... *A61K 8/25* (2013.01); *A61K 8/26* (2013.01); *A61K 8/891* (2013.01); *A61K 8/898* (2013.01); *A61K 8/965* (2013.01); *A61Q 1/00* (2013.01); *A61Q 1/10* (2013.01); *A61Q 1/12* (2013.01); *A61K 2800/31* (2013.01)

(58) Field of Classification Search
None
See application file for complete search history.

(56) References Cited

U.S. PATENT DOCUMENTS

2007/0020216 A1* 1/2007 Reinhart .................. A61K 8/64
424/70.7
2007/0053859 A1 3/2007 Bui et al.

FOREIGN PATENT DOCUMENTS

| FR | 2 881 643 A1 | | 8/2006 | |
| FR | 2881643 | * | 8/2006 | ............. A61K 8/965 |
| FR | 2 918 272 A1 | | 1/2009 | |
| FR | 2 924 929 A1 | | 6/2009 | |
| WO | WO 97/30126 A1 | | 8/1997 | |
| WO | WO 99/31184 A1 | | 6/1999 | |
| WO | WO 2010054921 | * | 5/2010 | ............. A61Q 15/00 |
| WO | WO 2010105952 | * | 9/2010 | ............... A61K 8/19 |

OTHER PUBLICATIONS

Face Powder. http://www.mybodybeautiful.co.uk/Beauty/Makeup/Powder.htm. Published Oct. 9, 2004.*
Talc. https://web.archive.org/web/20060222033010/http://www.mineralszone.com/minerals/talc.html. Published Feb. 22, 2006.*
Products Lineup. http://www.jigen.co.jp/products/raw.html. Published 2008.*
International Search Report issued in International Application No. PCT/IB2011/054047 dated Dec. 1, 2011.
Written Opinion of the International Searching Authority issued in International Application No. PCT/IB2011/054047 dated Dec. 1, 2011.

* cited by examiner

Primary Examiner — Jyothsna A Venkat
(74) Attorney, Agent, or Firm — Oliff PLC

(57) ABSTRACT

The present invention relates to a solid cosmetic makeup and/or care composition in the form of a powder comprising, in a physiologically acceptable medium, at least: —a fatty phase containing at least one silicone polyamide and a silicone resin, and —at least one pulverulent phase containing at least perlite.

3 Claims, No Drawings

SOLID COSMETIC MAKEUP COMPOSITION

The present invention relates to the field of solid cosmetic care and/or makeup compositions.

The galenical forms conventionally adopted for solid compositions are generally loose, pressed or compact powders. As nonlimiting illustrations of the solid galenical forms more particularly considered in the field of makeup, mention may be made especially of loose, pressed or compact powders such as foundations, face powders and eyeshadows.

The function of the abovementioned powders is mainly to give color, mattness and even, for those more particularly intended for facial skin, to improve the wear property of a foundation or, if used alone, to give coverage (powder foundation).

These galenical forms are particularly appreciated by users with regard to their lightness, softness, tack-free aspect or non-greasy feel.

In general, these compositions combine a pulverulent phase that is generally predominant with a binder phase usually featured by a liquid fatty phase. The pulverulent phase is formed essentially of fillers combined with pigments, the amount of these pigments being modified to afford the desired makeup effect, generally a color effect. As regards the fillers, it is generally preferred to choose materials that are capable of showing absorbing and/or adsorbing capacity with regard to the associated binder phase. To this end, materials of porous or lamellar structure such as talc, nacre powders, titanium oxide or zinc oxide prove to be particularly advantageous.

However, these materials are generally white and, in this respect, are liable to affect the staying power of the composition containing them with regard precisely to their interaction with the binder phase. Now, defective staying power over time may be reflected in particular by poor color fastness over time. Thus, poor staying power may be characterized by a modification of the color (color change or fading) generally following an interaction of these fillers with the binder phase or even with the sebum and/or sweat secreted by the skin. These absorption and/or adsorption phenomena are all the more manifest when these fillers are present in large amounts.

What is more, when these fillers at least partly feature a significant amount of nacre powder, the natural radiance of this material is detrimental to the production of a matt effect with the corresponding makeup composition.

One object of the present invention is thus to propose a cosmetic care and/or makeup composition that satisfies consumers' sensory expectations, i.e. lightness and softness of feel, in terms of comfort, which is endowed with good staying power especially in terms of the color over time, and which proves to be suitable for affording a matt makeup effect.

For the purposes of the invention, the term "staying power" means the color fastness over time and also the absence of streaks (i.e. staying power of the product on the skin).

The inventors have found, unexpectedly, that the use of a specific filler makes it possible to obtain compositions that are satisfactory in these terms.

Unexpectedly, the inventors have found that, the use of a specific filler makes it possible to obtain compositions which give satisfaction in these terms.

Consequently, according to a first aspect, the present invention relates to a solid cosmetic makeup and/or care composition comprising, in a physiologically acceptable medium, at least:

a fatty phase containing at least one silicone polyamide and a silicone resin, and a pulverulent phase containing at least perlite.

More particularly, the compositions considered according to the invention are in the form of a powder. This powder may be loose, pressed or else compacted. Preferably, it is a loose powder or a pressed powder.

Perlite is a natural glass of volcanic origin, which is light gray or glossy black in color, resulting from the rapid cooling of lava, and which is in the form of small particles resembling pearls. When it is heated above 800° C., it has the particular feature of losing the water it contains and of taking a porous expanded form (representing from four to twenty times its initial volume), enabling it to absorb large amounts of oil.

Besides its conventional use in building materials, resulting from its low weight and its good insulating properties, it has already been suggested to use perlite in the cosmetics field.

Its oil-absorbing properties have thus been exploited in powders for manufacturing granules intended for skin exfoliation (WO 99/31184, WO 97/30126 and WO 97/30126). These exfoliant compositions are compositions intended to be rinsed off so as not to leave any perlite particles on the skin.

More recently, smaller perlite particles have been used in cosmetic care and/or makeup compositions. Thus, patent application FR 2 881 643 describes the use of perlite particles with a particle size distribution such that at least 50% of the particles are smaller than 25 µm in size, as matting agent in water-based cosmetic formulations.

On the other hand, to the inventors' knowledge, the combination of perlite with a fatty phase in accordance with the invention for the formulation of a solid cosmetic composition, in particular of powder type, has never been described.

According to one particular embodiment, the pulverulent phase is present in a proportion of at least 35% by weight relative to total weight of the composition.

According to another embodiment variant, this pulverulent phase is combined with the fatty phase in a pulverulent phase/fatty phase weight ratio ranging from 55/45 to 70/30.

Preferably, the silicone polyamide (SPA) and the silicone resin are used in an SPA/silicone resin weight ratio ranging from 0.25 to 1, better still from 0.4 to 0.8, preferably from 0.5 to 0.6 and in particular equal to 0.56.

More preferentially, these two compounds are used with at least 0.1% to 15%, better still from 2% to 10%, more particularly from 4% to 8% by weight of perlite relative to the total weight of the composition.

According to another embodiment variant, the pulverulent phase forming the composition of the invention may comprise, besides the perlite, an additional filler.

Preferably, the composition according to the invention comprising a fatty phase comprising at least one silicone polyamide is obtained by means of a specific process that affords a cosmetic composition of novel texture, namely a paste that is soft or in the form of chips, which has good elasticity. This texture allows a smooth, uniform film to be applied to keratin materials, and has good wear properties.

A subject of the present invention is also a process for making up or caring, in particular in cosmetics, for keratin materials and especially the eyelids, in which a composition as defined previously is applied to said keratin materials.

As emerges from the foregoing, the compositions considered according to the invention are solid.

The term "solid" characterizes the state of the composition at room temperature (25° C.) and at atmospheric pressure (760 mmHg).

Preferably, the composition according to the invention comprises less than 5% by weight and preferably less than 3% by weight of water relative to the total weight; preferably, the composition is free of water.

Preferably, the composition is an eyeshadow, an eyebrow composition, an eyeliner, a blusher or a face powder. Even more preferentially, the composition is a foundation, an eyeshadow or a blusher. It is more particularly a foundation.

Perlite

According to one advantageous embodiment, the perlite particles used according to the invention have a small particle size.

Thus, the perlite particles may preferably have a particle size distribution such that at least 50% of the particles are smaller than 25 µm in size.

Preferably, the perlite particles according to the invention have a particle size distribution such that at least 50% of the particles are smaller than 20 µm in size.

In addition, they preferentially have a particle size distribution such that 90% by weight of the particles are smaller than 55 µm and preferably smaller than 40 µm in size. It is moreover preferred for 90% by weight of the particles to be larger than 5 µm in size.

The amount of perlite particles used according to the invention may advantageously represent from 0.1% to 15% by weight, for example from 2% to 10% by weight, for example from 4% to 8% by weight, relative to the total weight of the composition.

The perlite particles that may be used according to the invention are especially commercially available from the company World Minerals Europe under the trade name Perlite P1430, Perlite P2550 or Perlite P2040. These particles are sold as matting agents for paints. They are in the form of a white powder with a crystalline silica content of less than 0.1% by weight.

As stated hereinabove, perlite forms all or part of the pulverulent phase of the composition.

Pulverulent Phase

A solid composition according to the invention advantageously has a content of pulverulent phase of greater than or equal to 35% by weight, in particular greater than or equal to 40% by weight and more particularly ranging from 45% to 80% by weight relative to its total weight.

According to one preferred variant, the perlite is present in a content ranging from 5% to 40% by weight, better still from 7% to 15% by weight and more particularly from 10% to 13% by weight relative to the total weight of the fillers.

According to one variant, the perlite is present in a content ranging from 5% to 25% by weight, better still from 5% to 12% and more particularly from 6% to 11% by weight relative to the total weight of the pulverulent phase.

Besides the perlite, this pulverulent phase may comprise one or more additional filler(s), and advantageously also at least one dyestuff, especially for the makeup compositions according to the invention.

However, the presence of additional filler is adjusted so as not to be detrimental to the properties precisely sought by the presence of perlite.

Fillers

The term "fillers" should be understood as meaning colorless or white, mineral or synthetic particles of any shape, which are insoluble in the medium of the composition, irrespective of the temperature at which the composition is manufactured.

The additional fillers may be chosen from fillers such as:

silica microspheres, especially of open porosity or, preferably, hollow silica microspheres, such as the products Silica Beads SB 700/HA or Silica Beads SB 700 from the company Maprecos; these microspheres may be impregnated with a cosmetic active agent;

microporous polymer microspheres, which have a structure similar to that of a sponge; they generally have a specific surface area of at least 0.5 $m^2/g$ and in particular of at least 1 $m^2/g$, said specific surface area having no upper limit other than that resulting from the practical possibility of making microspheres of very high porosity: the specific surface area may, for example, be up to 1000 $m^2/g$ or even more. Microspheres that may be mentioned include acrylic polymer microspheres, such as those made of crosslinked acrylate copolymer Polytrap 6603 Adsorber from the company RP Scherer, and those made of polymethyl methacrylate Micropearl M 100 from the company SEPPIC;

polyurethane powder such as the powder of a copolymer of hexamethylene diisocyante and of trimethylol hexyl lactone sold under the names Plastic Powder D-400 and T-7 by the company Toshiki;

polymer microcapsules that comprise a single closed cavity and form a reservoir, which may contain a liquid, especially a cosmetic active agent; they are prepared via known processes such as those described in patents U.S. Pat. No. 3,615,972 and EP-A-0 56219. They may be made, for example, of polymers or copolymers of ethylenically unsaturated acid, amine or ester monomers, of urea-formaldehyde polymers or of vinylidene chloride polymers or copolymers; by way of example, mention may be made of microcapsules made of methyl acrylate or methacrylate polymers or copolymers, or alternatively of copolymers of vinylidene chloride and of acrylonitrile; among these polymers, mention will be made especially of those containing 20-60% by weight of units derived from vinylidene chloride, 20-60% by weight of units derived from acrylonitrile and 0-40% by weight of other units such as units derived from an acrylic and/or styrene monomer; crosslinked acrylic polymers or copolymers may also be used;

elastomeric crosslinked organopolysiloxane spherical powders, described especially in document JP-A-02 243 612, such as those sold under the name Trefil Powder E-506C by the company Dow Corning;

the carnauba wax microbeads sold under the name Microcare 350® by the company Micro Powders and the paraffin wax microbeads sold under the name Microease 114S® by the company Micro Powders;

metal soaps in powder form. Among these soaps, mention may be made especially of metal soaps of fatty acids containing from 12 to 22 carbon atoms and in particular those containing from 12 to 18 carbon atoms. The metal of the metal soap may especially be zinc or magnesium. The fatty acid may be chosen especially from lauric acid, myristic acid, stearic acid and palmitic acid. The metal soaps that may be used include zinc laurate, magnesium stearate, magnesium myristate and zinc stearate, and mixtures thereof;

talcs or hydrated magnesium silicates, especially in the form of particles generally less than 40 µm in size;

micas or aluminosilicates of varied composition that are especially in the form of flakes from 2 to 200 µm and preferably 5-70 µm in size and from 0.1 to 5 µm and preferably 0.2-3 µm in thickness, these micas possibly being of natural origin (for example muscovite, margarite, roscoelite, lipidolite or biotite) or of synthetic origin;

clays such as sericites, which belong to the same chemical and crystalline class as muscovite;

kaolin or hydrated aluminum silicate, which is especially in the form of particles of isotropic forms generally less than 30 μm in size;

boron nitrides;

powders of tetrafluoroethylene polymers, such as Ceridust 9205 F from the company Clariant;

precipitated calcium carbonate, especially in the form of particles greater than 10 μm in size;

magnesium carbonate and magnesium hydrogen carbonate;

hydroxyapatite;

powders of non-expanded synthetic polymers, such as polyethylene, polyesters (for example polyethylene isophthalate or terephthalate) and polyamides (for example Nylon), in the form of particles less than 50 μm in size;

powders of spheronized, crosslinked or non-crosslinked synthetic polymers, for instance polyamide powders such as poly-β-alanine powder or Nylon powder, for example Orgasol powder from the company Atochem, polyacrylic acid or polymethacrylic acid powder, powders of polystyrene crosslinked with divinylbenzene, and silicone resin powders, and bismuth oxychloride powders, powders of organic materials of natural origin, for instance starches, especially corn starch, wheat starch or rice starch;

and mixtures thereof.

Advantageously, a composition according to the invention is totally devoid of filler having a refractive index which is greater than 1.8.

As representatives of such fillers, mention may especially be made of titanium oxides, zinc oxides and bismuth oxychloride powders.

The additional fillers may be present in a content ranging from 0.1% to 60% by weight and preferably ranging from 1% to 55% by weight relative to the total weight of the composition.

According to one advantageous variant, a composition according to the invention may contain as filler, besides the perlite, a polyurethane powder and/or mica. Preferably, the composition comprises perlite, polyurethane powder and optionally mica.

Advantageously, a composition according to the invention may comprise a total content of fillers ranging from 10% to 60% by weight, preferably ranging from 12% to 60% by weight and preferentially ranging from 15% to 60% by weight, relative to the total weight of the composition.

As stated above, a composition according to the invention may also comprise, in its pulverulent phase, a coloring agent.

The coloring agent or dyestuff according to the invention is chosen from pigments, nacres and reflective particles, and mixtures thereof.

According to one embodiment variant, a composition according to the invention may comprise a pulverulent phase formed from a large amount, for example more than 35% or even 40% by weight, of coloring agents, featured especially by pigments and/or nacres. In such an embodiment, the amount of associated filler including perlite may then range from 10% to 35% by weight or even from 10% to 25% by weight relative to the total weight of the composition.

Pigments

The term "pigments" should be understood as meaning white or colored, mineral or organic particles of any form, which are insoluble in the physiological medium and are intended to color the composition.

The pigments may be white or colored, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminum powder and copper powder.

The organic pigments may be chosen from the materials below, and mixtures thereof:

cochineal carmine, organic pigments of azo dyes, anthraquinone dyes, indigoid dyes, xanthene dyes, pyrene dyes, quinoline dyes, triphenylmethane dyes and fluorane dyes.

Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the publication "International Cosmetic Ingredient Dictionary and Handbook", 1997 edition, pages 371 to 386 and 524 to 528, published by "The Cosmetic, Toiletries and Fragrance Association".

According to a preferred variant, a composition according to the invention may comprise a total content of pigments ranging from 0.1% to 70% by weight, preferably ranging from 0.5% to 65% by weight and preferentially ranging from 1% to 60% by weight, relative to the total weight of the composition.

When it is a makeup product, a pigment content ranging from 1% to 40% by weight, preferably from 5% to 30% by weight and in particular from 10% to 25% by weight relative to the total weight of said composition will generally be used.

According to another embodiment variant, a composition according to the invention may be free of pigments.

The pulverulent phase according to the invention may also comprise, or may even be formed from, nacres and/or reflective particles.

The term "nacre" should be understood as meaning colored particles of any form, which may or may not be iridescent, especially produced by certain molluscs in their shell, or alternatively synthesized, and which have a color effect via optical interference.

Examples of nacres that may be mentioned include nacreous pigments such as titanium mica coated with an iron oxide, mica coated with bismuth oxychloride, titanium mica coated with chromium oxide, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery color or tint.

As illustrations of nacres that may be introduced as interference pigments into the first composition, mention may be made especially of the gold-colored nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P0.004X0.004 (silver flakes).

According to one particular variant, the compositions according to the invention may comprise from 0 to 65%, for example 30% to 65% and better still 40% to 60% by weight of nacres. More preferentially, they contain less than 70% by weight of nacres. According to one particular embodiment, the composition according to the invention is free of nacres.

Finally, the coloring agent according to the invention may be chosen from reflective particles.

The term "reflective particles" denotes particles whose size, structure, especially the thickness of the layer(s) of which they are made and their physical and chemical nature, and surface state allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the coloration effect generated by the coloring agents with which they are combined, and more particularly so as to optimize this effect in terms of color yield. They may more particularly have a yellow, pink, red, bronze, orange, brown, gold and/or coppery color or tint.

These particles may have varied forms and may especially be in platelet or globular form, in particular spherical.

Irrespective of their form, the reflective particles may or may not have a multilayer structure, and, in the case of a multilayer structure, for example at least one layer of uniform thickness, especially a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be a monomaterial, multimaterial, organic and/or mineral substrate.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Particles comprising a metallic substrate such as silver, aluminum, iron, chromium, nickel, molybdenum, gold, copper, zinc, tin, manganese, steel, bronze or titanium, may also be used, said substrate being coated with at least one layer of at least one metal oxide such as titanium oxide, aluminum oxide, iron oxide, cerium oxide, chromium oxide or silicon oxides, and mixtures thereof.

Examples that may be mentioned include aluminum powder, bronze powder or copper powder coated with $SiO_2$ sold under the name Visionaire by the company Eckart.

Preferably, the pulverulent phase comprises at least one compound chosen from:
organic pigments such as, for example:
the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11, mineral pigments such as:
iron oxide, zirconium oxide, cerium oxide, iron oxide or chromium oxide,
ferric blue, manganese violet, ultramarine blue, pink or violet, chromium hydrate or chromium hydroxide,
nacres such as, for example:
mica coated with titanium oxide, mica coated with titanium oxide and iron oxide, and mica coated with an amino acid such as lauroyl lysine,
polyethylene terephthalate flakes,
sericite,
and mixtures thereof,
reflective particles such as, for example:
particles comprising a borosilicate substrate coated with a metallic layer.

Fatty Phase

As emerges from the foregoing, a cosmetic composition according to the invention comprises at least one fatty phase as binder.

This liquid fatty phase is advantageously present in a proportion of at least 15% by weight relative to the total weight of said composition, and preferably in a proportion of from 30% to 45% by weight and in particular from 35% to 42% by weight relative to the total weight of the composition.

This fatty phase may be formed partially or totally from the silicone polyamide and the silicone resin required according to the invention.

Silicone Polyamide

As indicated previously, the compositions according to the invention comprise at least one silicone polyamide.

The silicone polyamides of the composition are preferably solid at room temperature (25° C.) and atmospheric pressure (760 mmHg).

For the purposes of the invention, the term "polymer" means a compound containing at least two repeating units, preferably at least three repeating units and better still ten repeating units.

The silicone polyamides of the composition of the invention may be polymers of the polyorganosiloxane type, for instance those described in documents U.S. Pat. No. 5,874,069, U.S. Pat. No. 5,919,441, U.S. Pat. No. 6,051,216 and U.S. Pat. No. 5,981,680. According to the invention, the silicone polymers may belong to the following two families:

(1) polyorganosiloxanes comprising at least two amide groups, these two groups being located in the polymer chain, and/or (2) polyorganosiloxanes comprising at least two amide groups, these two groups being located on grafts or branches.

A) According to a first variant, the silicone polymers are polyorganosiloxanes as defined above in which the amide units are located in the polymer chain.

The silicone polyamides may be more particularly polymers comprising at least one unit corresponding to the general formula I:

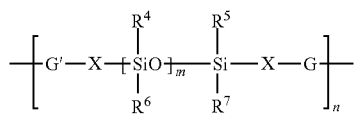

(I)

1) in which: G' represents C(O) when G represents —C(O)—NH—Y—NH—, and G' represents —NH— when G represents —NH—C(O)—Y—C(O)—, 2) $R^4$, $R^5$, $R^6$ and $R^7$, which may be identical or different, represent a group chosen from:
linear, branched or cyclic, saturated or unsaturated, $C_1$ to $C_{40}$ hydrocarbon-based groups, possibly containing in their chain one or more oxygen, sulfur and/or nitrogen atoms, and possibly being partially or totally substituted with fluorine atoms,
$C_6$-$C_{10}$ aryl groups, optionally substituted with one or more $C_1$-$C_4$ alkyl groups,
polyorganosiloxane chains possibly containing one or more oxygen, sulfur and/or nitrogen atoms, 3) the groups X, which may be identical or different, represent a linear or branched $C_1$ to $C_{30}$ alkylenediyl group, possibly containing in its chain one or more oxygen and/or nitrogen atoms;

4) Y is a saturated or unsaturated $C_1$ to $C_{50}$ linear or branched alkylene, arylene, cycloalkylene, alkylarylene or arylalkylene divalent group, which may comprise one or more oxygen, sulfur and/or nitrogen atoms, and/or may bear as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with one to three $C_1$ to $C_3$ alkyl, $C_1$ to $C_3$ hydroxyalkyl and $C_1$ to $C_6$ aminoalkyl groups, or 5) Y represents a group corresponding to the formula:

in which:
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
$R^8$ represents a linear or branched $C_{10}$-$C_{50}$ alkyl group or a polyorganosiloxane chain, possibly comprising one or more ester, amide, urethane, thiocarbamate, urea, thiourea and/or sulfonamide groups, which may possibly be linked to another chain of the polymer;

6) n is an integer ranging from 2 to 500 and preferably from 2 to 200, and m is an integer ranging from 1 to 1000, preferably from 1 to 700 and better still from 6 to 200.

According to the invention, 80% of the groups $R^4$, $R^5$, $R^6$ and $R^7$ of the polymer are preferably chosen from methyl, ethyl, phenyl and 3,3,3-trifluoropropyl groups. According to another embodiment, 80% of the groups $R^4$, $R^5$, $R^6$ and $R^7$ of the polymer are methyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) branched $C_{30}$ to $C_{56}$ alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

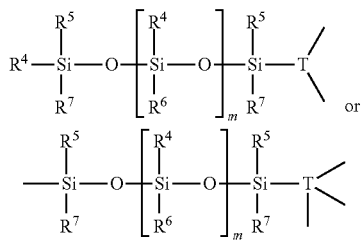

in which $R^4$, $R^5$, $R^6$, $R^7$, T and m are as defined above.

B) According to the second variant, the silicone polyamides may be polymers comprising at least one unit corresponding to formula (II):

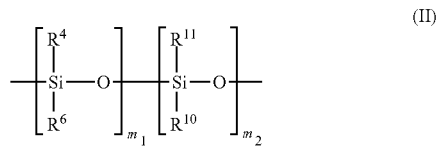

in which:

$R^4$ and $R^6$, which may be identical or different, are as defined above for formula (I), $R^{10}$ represents a group as defined above for $R^4$ and $R^6$, or represents a group of formula —X-G"—$R^{12}$ in which X is as defined above for formula (I) and $R^{12}$ represents a hydrogen atom or a linear, branched or cyclic, saturated or unsaturated, $C_1$-$C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$-$C_4$ alkyl groups, and G" represents —C(O)NH— and —HN—C(O)—, $R^{11}$ represents a group of formula —X-G"-$R'^2$ in which X, G" and $R^{12}$ are as defined above, $m_1$ is an integer ranging from 1 to 998, and $m_2$ is an integer ranging from 2 to 500.

According to the invention, the silicone polymer may be a homopolymer, i.e. a polymer comprising several identical units, in particular units of formula (I) or of formula (II).

According to the invention, it is also possible to use a polymer consisting of a copolymer comprising several different units of formula (I), i.e. a polymer in which at least one of the groups $R^4$, $R^5$, $R^6$, $R^7$, X, G, Y, m and n is different in one of the units. The copolymer may also be formed from several units of formula (II), in which at least one of the groups $R^4$, $R^6$, $R^{10}$, $R^{11}$, $m_1$ and $m_2$ is different in at least one of the units.

It is also possible to use a polymer comprising at least one unit of formula (I) and at least one unit of formula (II), the units of formula (I) and the units of formula (II) possibly being identical to or different than each other.

According to one variant of the invention, it is also possible to use a silicone polyamide furthermore comprising at least one hydrocarbon-based unit comprising two groups capable of establishing hydrogen interactions, chosen from ester, sulfonamide, carbamate, thiocarbamate, urea, urethane, thiourea, oxamido, guanidino and biguanidino groups, and combinations thereof.

These copolymers may be block polymers or grafted polymers.

In formulae (I) and (II), the alkylene group representing X or Y can optionally contain in its alkylene part at least one of the following components:

1) one to five amide, urea, urethane or carbamate groups, 2) a $C_5$ or $C_6$ cycloalkyl group, and 3) a phenylene group optionally substituted with 1 to 3 identical or different $C_1$ to $C_3$ alkyl groups.

In formulae (I) and (II), the alkylene groups may also be substituted with at least one component chosen from the group formed from:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

In these formulae (I) and (II), Y may also represent:

in which $R^8$ represents a polyorganosiloxane chain and T represents a group of formula:

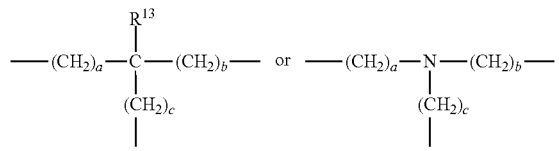

in which a, b and c are, independently, integers ranging from 1 to 10, and $R^{13}$ is a hydrogen atom or a group such as those defined for $R^4$, $R^5$, $R^6$ and $R^7$.

In formulae (I) and (II), $R^4$, $R^5$, $R^6$ and $R^7$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different units of formula (I) or (II).

Thus, the polymer may be a polyamide containing several units of formula (I) or (II) of different lengths, i.e. a polyamide corresponding to formula (III):

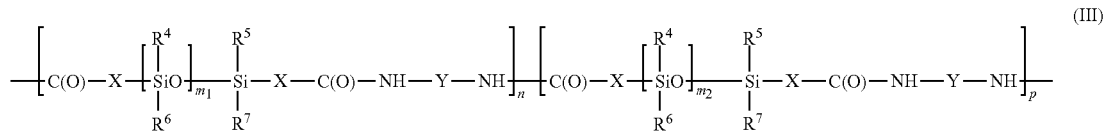

in which X, Y, n and $R^4$ to $R^7$ have the meanings given above, $m_1$ and $m_2$, which are different, are chosen in the range from 1 to 1000, and p is an integer ranging from 2 to 300.

In this formula, the units may be structured to form either a block copolymer, or a random copolymer or an alternating copolymer. In this copolymer, the units may be not only of different lengths, but also of different chemical structures, for example containing different groups Y. In this case, the polymer may correspond to formula (IV):

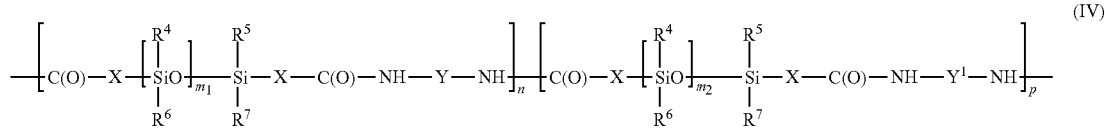

in which $R^4$ to $R^7$, X, Y, $m_1$, $m_2$, n and p have the meanings given above and $Y^1$ is different than Y but chosen from the groups defined for Y. As previously, the various units may be structured to form either a block copolymer, or a random copolymer or an alternating copolymer.

In this first embodiment of the invention, the silicone polymer may also consist of a grafted copolymer. Thus, the polyamide containing silicone units may be grafted and optionally crosslinked with silicone chains containing amide groups. Such polymers may be synthesized with trifunctional amines.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to one embodiment variant of the invention, a copolymer of silicone polyamide and of hydrocarbon-based polyamide, or a copolymer comprising units of formula (I) or (II) and hydrocarbon-based polyamide units, may be used. In this case, the polyamide-silicone units may be located at the ends of the hydrocarbon-based polyamide.

Advantageously, the composition comprises at least one polyamide/polydimethylsiloxane polymer, especially a polymer of general formula (I) with an index m of greater than 50, in particular greater than 75 and especially of about 100.

Advantageously, the silicone polyamide of formula (I) has a weight-average molecular mass ranging from 10 000 to 500 000 g/mol.

More preferably, X and Y independently represent a group chosen from linear $C_1$-$C_{20}$ and preferably $C_1$-$C_{10}$ alkylene groups.

As examples of polymers that may be used, mention may be made of one of the silicone polyamides obtained in accordance with Examples 1 to 3 of document U.S. Pat. No. 5,981,680.

Preferably, the nylon-611/dimethicone copolymer sold under the reference DC 2-8179 by Dow Corning is used as silicone polyamide.

The polymers and copolymers used in the composition of the invention advantageously have a temperature of transition from the solid state to the liquid state ranging from 45° C. to 190° C. Preferably, they have a temperature of transition from the solid state to the liquid state ranging from 70 to 130° C. and better still from 80° C. to 105° C.

The silicone polyamide may be present in the composition in a total content ranging from 0.5% to 45% by weight relative to the total weight of the composition, preferably ranging from 1% to 30% by weight and better still ranging from 2% to 20% by weight relative to the total weight of said composition.

Silicone Resin

Examples of these silicone resins that may be mentioned include:

siloxysilicates, which may be trimethylsiloxysilicates of formula $[(CH_3)_3SiO]_x(SiO_{4/2})_y$ (units MQ) in which x and y are integers ranging from 50 to 80, polysilsesquioxanes of formula $(CH_3SiO_{3/2})_x$ (units T) in which x is greater than 100 and at least one of the methyl radicals of which may be substituted with a group R as defined above, polymethylsilsesquioxanes, which are polysilsesquioxanes in which none of the methyl radicals is substituted with another group. Such polymethylsilsesquioxanes are described in document U.S. Pat. No. 5,246,694.

As examples of commercially available polymethylsilsesquioxane resins, mention may be made of those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10 000 g/mol, or by the company Shin-Etsu under the reference KR-220L, which are composed of units T of formula $CH_3SiO_{3/2}$ and contain Si—OH (silanol) end groups, under the reference KR-242A, which comprise 98% of units T and 2% of dimethyl units D and contain Si—OH end groups, or under the reference KR-251, comprising 88% of units T and 12% of dimethyl units D and contain Si—OH end groups.

Siloxysilicate resins that may be mentioned include trimethyl siloxysilicate resins (TMS) optionally in the form of powders. Such resins are sold under the reference SR1000 by the company Momentive Performance Materials or under the reference TMS 803 by the company Wacker. Mention may also be made of trimethyl siloxysilicate resins sold in a solvent such as cyclomethicone, sold under the name KF-7312J by the company Shin-Etsu or DC 749 and DC 593 by the company Dow Corning.

More particularly, a siloxysilicate resin, preferably a trimethyl siloxysilicate resin, is used as silicone resin.

Advantageously, the silicone resin, for instance the trimethyl siloxysilicate resin, is present in a content ranging from 0.5% to 30%, or better still from 1% to 25% or even better still from 5% to 25% relative to the total weight of the composition.

Preferably, the silicone resin, and especially the trimethyl siloxysilicate resin, is present in a ratio such that the silicone polyamide/silicone resin mass proportion is between 0.25 and 1 and preferably between 0.33 and 1.

Preferably, nylon-611/dimethicone is used as silicone polyamide and a trimethyl siloxysilicate resin is used as silicone resin.

The fatty phase of the composition according to the invention may also comprise at least one oil.

According to a preferred variant, the composition according to the invention comprises at least one silicone oil.

In one preferred embodiment, the composition according to the invention comprises at least one volatile oil.

According to one preferred embodiment, the composition according to the invention comprises at least one silicone oil, especially a cyclohexadimethylsiloxane.

The composition may also comprise at least one nonvolatile oil. According to one embodiment, the composition according to the invention is free of nonvolatile oil.

The oil(s) may be present in a content ranging from 1% to 45% by weight and preferably from 5% to 40% by weight relative to the total weight of the composition.

For the purposes of the invention, the term "volatile oil" means an oil that is capable of evaporating on contact with the skin or the keratin fiber in less than one hour, at room temperature and atmospheric pressure. The volatile organic solvent(s) and volatile oils of the invention are volatile organic solvents and cosmetic oils that are liquid at room temperature, with a nonzero vapor pressure at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

The term "nonvolatile oil" means an oil that remains on the keratin material at room temperature and atmospheric pressure for at least several hours and that especially has a vapor pressure of less than $10^{-3}$ mmHg (0.13 Pa).

These oils may be hydrocarbon-based oils, silicone oils or fluoro oils, or mixtures thereof.

The term "hydrocarbon-based oil" means an oil mainly containing hydrogen and carbon atoms and optionally oxygen, nitrogen, sulfur or phosphorus atoms. The volatile hydrocarbon-based oils may be chosen from hydrocarbon-based oils containing from 8 to 16 carbon atoms, and especially branched $C_8$-$C_{16}$ alkanes, for instance $C_8$-$C_{16}$ isoalkanes of petroleum origin (also known as isoparaffins), for instance isododecane (also known as 2,2,4,4,6-pentamethylheptane), isodecane and isohexadecane, for example the oils sold under the trade names Isopar or Permethyl, branched $C_8$-$C_{16}$ esters and isohexyl neopentanoate, and mixtures thereof. Other volatile hydrocarbon-based oils, for instance petroleum distillates, especially those sold under the name Shell Solt by the company Shell, may also be used.

The volatile hydrocarbon-based oils may also be chosen from linear $C_8$-$C_{16}$ alkanes. Examples of linear $C_8$-$C_{16}$ alkanes that may be mentioned include n-nonadecane ($C_9$), n-decane ($C_{10}$), n-undecane ($C_{11}$), n-dodecane ($C_{12}$), n-tridecane ($C_{13}$), n-tetradecane ($C_{14}$), n-pentadecane ($C_{15}$) and n-hexadecane ($C_{16}$), and mixtures thereof, and in particular the mixture of n-undecane ($C_{11}$) and of n-tridecane ($C_{13}$) sold under the reference Cetiol UT by the company Cognis.

Volatile oils that may also be used include volatile silicones, for instance volatile linear or cyclic silicone oils, especially those with a viscosity 8 centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to one embodiment variant, a composition according to the invention contains at least one volatile silicone oil, which is especially cyclic, and in particular an oil such as cyclohexadimethylsiloxane.

Mention may also be made of linear volatile alkyltrisiloxane oils of general formula (I):

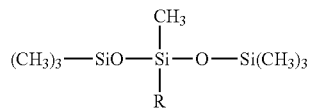

in which R represents an alkyl group containing from 2 to 4 carbon atoms, of which one or more hydrogen atoms may be substituted with a fluorine or chlorine atom.

Among the oils of general formula (I) that may be mentioned are:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Volatile fluoro solvents such as nonafluoromethoxybutane or perfluoromethylcyclopentane may also be used.

Preferably, the composition comprises a content of volatile oil ranging from 1% to 45% by weight and preferably from 5% to 40% by weight relative to the total weight of the composition.

Advantageously, a composition according to the invention may comprise at least 5% by weight, especially at least 10% by weight or even at least 15% by weight of volatile silicone oil(s).

The composition may also comprise at least one nonvolatile oil, chosen especially from nonvolatile hydrocarbon-based oils and/or silicone oils and/or fluoro oils.

Nonvolatile hydrocarbon-based oils that may especially be mentioned include:
hydrocarbon-based oils of plant origin, such as triglycerides consisting of fatty acid esters of glycerol, the fatty acids of which may have varied chain lengths from $C_4$ to $C_{24}$, these chains possibly being linear or branched, and saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame seed oil, marrow oil, rapeseed oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by the company Stéarineries Dubois or those sold under the names Miglyol 810, 812 and 818 by the company Dynamit Nobel;

synthetic ethers containing from 10 to 40 carbon atoms;

linear or branched hydrocarbons of mineral or synthetic origin, such as petroleum jelly, polydecenes, hydrogenated polyisobutene such as parleam, and squalane, and mixtures thereof;

synthetic esters such as oils of formula $R_1COOR_2$ in which $R_1$ represents a linear or branched fatty acid residue containing from 1 to 40 carbon atoms and $R_2$ represents an in particular branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$-$C_{15}$ alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;

fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

higher fatty acids such as oleic acid, linoleic acid or linolenic acid;

carbonates;

acetals;

citrates;

and mixtures thereof.

The nonvolatile silicone oils that may be used in the compositions according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

The fluoro oils that may be used in the invention are, in particular, fluorosilicone oils, fluoro polyethers or fluorosilicones, as described in document EP-A-847 752.

The composition according to the invention may comprise an aqueous phase. However, this aqueous phase must be used in an amount that is compatible with the pulverulent galenical form required according to the invention.

The water may be a floral water such as cornflower water and/or a mineral water such as Vittel water, Lucas water or La Roche Posay water and/or a spring water.

The aqueous phase may also comprise a polyol that is miscible with water at room temperature (25° C.) chosen especially from polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers and mixtures thereof.

Glycerol is most particularly suitable for use as a polyol.

The composition according to the invention may also comprise a polyol that is miscible with water at room temperature in a content ranging from 1% to 20% by weight and preferably ranging from 3% to 15% by weight relative to the total weight of the composition. Such polyols may promote the moisturization of the surface of the skin on which the composition is applied.

In addition, the composition according to the invention may comprise a monoalcohol containing from 2 to 6 carbon atoms such as ethanol or isopropanol, especially in a content ranging from 0.01% to 10% by weight and preferably ranging from 1% to 7% by weight relative to the total weight of the composition.

Preferably, the composition according to the invention comprises less than 5% by weight and preferably less than 3% by weight of water relative to the total weight; preferably, the composition is free of water.

The composition may comprise other ingredients (adjuvants) usually used in cosmetics, such as preserving agents, cosmetic active agents, moisturizers, UV screening agents, thickeners, surfactants and fragrances.

Needless to say, a person skilled in the art will take care to select the optional adjuvant(s) added to the composition according to the invention such that the advantageous properties intrinsically associated with the composition in accordance with the invention are not, or are not substantially, adversely affected by the envisioned addition.

According to another aspect, the invention also relates to a cosmetic assembly comprising:

i) a container delimiting a compartment, said compartment being closed by a closing member; and ii) a composition in accordance with the invention placed inside said compartment.

The container may be in any suitable form. It may especially be a bottle, a tube, a jar, a case, a can, a sachet or a box.

The closing member may be in the form of a removable stopper, a lid, a cap, a tear-off strip or a capsule, especially of the type comprising a body attached to the container and a cover cap articulated on the body. It may also be in the form of a member that selectively closes the container, especially a pump or a valve, for instance a clapper.

Preferably, the composition is inside a leaktight container.

Preparation Process

The composition according to the invention is preferably prepared according to the following procedure:

A formulation base comprising the silicone polyamide and the silicone resin is prepared. This base may also comprise one or more oils, especially volatile oils, and also a gelling agent.

This formulation base is then mixed with a fatty phase, especially a volatile or nonvolatile silicone oil, using a blender or an extruder.

Preferably, the process comprises at least one step of controlled shear of all of the ingredients of the composition, advantageously at a temperature greater than or equal to the solid-liquid transition temperature of the silicone polymer.

Any equipment or equipment combination for controlling a mechanical action that will blend the product gradually as it is prepared, such as processes functioning continuously of scraped-surface exchanger type, or preferably of blender/twin-screw extruder type (referred to for simplicity as "extruder" in the rest of the present document) is suitable for use in the process according to the invention.

Extruders of blender/twin-screw extruder type are preferably used, these extruders being composed of the following elements:
- at least two jackets independently temperature-regulated to a temperature ranging from 10° C. to 300° C.,
- two corotating axles composed of screw elements, each element having a shape that provides the desired mixing function in the corresponding temperature zone,
- devices for metering and introducing the various phases,
- a variable-speed motor, for modulating the intensity of the shear as a function of the spin speed of the screws.

When the process according to the invention is performed in a blender/extruder, the various ingredients may be incorporated at different temperatures in the course of the blending during cooling, at a temperature that is compatible with their stability.

As equipment for performing the invention, mention will be made especially, without limiting the invention to these machines, of the models BC-21 and BC-45 from the company Clextral, or the model Prism Eurolab from the company ThermoRheo.

The examples that follow are given as nonlimiting illustrations of the present invention. The percentages are weight percentages.

EXAMPLES 1 TO 4: EYESHADOWS

| | Formulation base: | |
|---|---|---|
| A | Isododecane | 51.5% by weight |
| A | Trimethyl siloxysilicate resin (SR1000 from Momentive Performance Materials) | 31% by weight |
| B | Nylon-611/Dimethicone copolymer (Dow Corning 2-8179 Gellant from Dow Corning) | 17.5 by weight |

The resin is mixed with part of the isododecane, and the mixture is allowed to swell.

Next, the silicone polyamide (phase B) is mixed with phase A, while stirring using a Moritz blender or under vigorous stirring with a Rayneri blender.

The formulation base is thus obtained.

| | Eyeshadows: | | | |
|---|---|---|---|---|
| | Example 1 (weight %) | Example 2 (weight %) | Example 3 (weight %) | Example 4 (weight %) |
| Perlite | 6 | 6 | 4 | 6 |
| PIGMENTS | 13 | 13.4 | 30 | — |
| Mica-titanium oxide-brown, black iron oxides (Cloisonne Nu Antique Bronze from Engelhard) | | | | |
| Mica-titanium oxide (Flamenco Orange 320 C from Engelhard) | | | | |
| Lauroyl lysine-coated mica (Mearlmica Treated SVA from Engelhard) | 4 | 4 | 4 | 4 |
| N-Lauroyl-L-lysine (Amihope LL from Ajinomoto) | — | — | 5 | — |
| Mica (Mearlmica CF from BASF Personal Care Ingredients) | 34.5 | 34 | 14.5 | — |
| Mica (Flamenco Pearl 110C from BASF Personal Care Ingredients) | — | — | — | 12 |
| Borosilicate (Ronastar Noble Sparks SQ from Merck) | — | — | — | 13 |
| PET (0.004 HEX CTD. Silver Poly Flake from Glitterex) | — | — | — | 14 |
| Aluminum (Cosmetic metallic powder Visionaire Bright Silver Sea from Eckart) | — | — | — | 8.5 |
| Hexamethylene diisocyanate/trimethylol hexyl lactone copolymer powder containing silica 10-15 µm (Plastic Powder D 400 from Toshiki Pigment) | 5.5 | 5.6 | 5.5 | 5.5 |
| Cyclohexadimethylsiloxane (viscosity: 8 cSt) (Dow Corning 246 Fluid from Dow Corning) | 18.25 | 18.25 | 18.25 | 18.25 |
| FORMULATION BASE: Trimethyl siloxysilicate resin (SR1000 from Momentive Performance Materials) Nylon-611/Dimethicone copolymer (Dow Corning 2-8179 Gellant from Dow Corning) Isopropyl alcohol Isododecane | 18.25 | 18.25 | 18.25 | 18.25 |
| Caprylyl glycol (Dermosoft Octiol from Dr. Straetmans) | 0.5 | 0.5 | 0.5 | 0.5 |

The compositions of Examples 1 to 4 are obtained according to the following protocol:
the formulation base is mixed with the silicone oil;
finally, the composition forming the pulverulent phase is added, and the mixture is placed in an extruder.

EXAMPLE 5: HEALTHY-COMPLEXION FORMULATION

The composition of Example 5 is obtained according to the protocol indicated above.

|  | Example 5 (weight %) |
|---|---|
| Perlite | 6 |
| Lauroyl lysine-coated mica (Mearlmica Treated SVA from Engelhard) | 4 |
| Red iron oxide (SUN) and talc (Val Chisone Luzenac) 70/30 dispersion | 2 |
| Yellow iron oxide (SUN) and talc (Val Chisone Luzenac) 70/30 dispersion | 1 |
| Black iron oxide (SUN) and talc (Val Chisone Luzenac) 70/30 dispersion | 1 |
| Mica (Mearlmica CF from BASF Personal Care Ingredients) | 43.5 |
| Hexamethylene diisocyanate/trimethylol hexyl lactone copolymer powder containing silica 10-15 µm (Plastic Powder D 400 from Toshiki Pigment) | 5.5 |
| Cyclohexadimethylsiloxane (viscosity: 8 cSt) (Dow Corning 246 Fluid from Dow Corning) | 18.25 |
| FORMULATION BASE: Trimethyl siloxysilicate resin (SR1000 from Momentive Performance Materials) Nylon-611/Dimethicone copolymer (Dow Corning 2-8179 Gellant from Dow Corning) Isopropyl alcohol Isododecane | 18.25 |
| Caprylyl glycol (Dermosoft Octiol from Dr. Straetmans) | 0.5 |

The invention claimed is:

1. A solid cosmetic makeup and/or care composition in the form of a powder comprising, in a physiologically acceptable medium, at least:
a fatty phase containing silicone polyamide and a silicone resin, and wherein the silicone polyamide is nylon-611/dimethicone copolymer and silicone resin is trimethyl siloxysilicate resin, wherein the nylon-611/dimethicone copolymer is present in amount of 2-20% by weight of the composition and trimethyl siloxysilicate resin is present in amount of 5-25% by weight of the composition wherein the weight ratio of nylon-611/dimethicone copolymer to the trimethyl siloxysilicate resin is 0.33-1
pulverulent phase containing in an amount of 4-8% by weight of the composition, the fatty phase comprises isododecane in an amount of 5-40% by weight of the composition, wherein the pulverulent phase is combined with the fatty phase in a pulverulent phase/fatty phase weight ratio ranging from 55/45 to 70/30, the cosmetic makeup composition further comprises:
additional fillers in an amount of 15-60% by weight of the composition, wherein the fillers are mixture of mica, iron oxide and titanium oxide,
a polyol having from 2-20 carbon atoms in an amount of 3-15% by weight of the composition,
wherein the composition is free of water perlite
wherein the silicone polyamide is a nylon-611/dimethicone copolymer and the silicone resin is a trimethyl siloxysilicate resin,
wherein the fatty phase further comprises at least one branched $C_8$-$C_{16}$ alkane, and
wherein the solid cosmetic makeup and/or care composition comprises from 0.1% to 15% by weight of perlite relative to the total weight of the composition and from 5% to 25% by weight of perlite relative to the total weight of the pulverulent phase, and wherein the pulverulent phase is present in a proportion of at least 35% by weight relative to the total weight of the composition.

2. The solid cosmetic makeup and/or care composition as claimed in claim 1, which is in the form of a loose powder or a pressed powder.

3. Method for making up keratin material according to claim 1, the method comprising applying the solid make up composition to keratin material.

* * * * *